(12) United States Patent
Koizumi et al.

(10) Patent No.: US 9,339,778 B2
(45) Date of Patent: May 17, 2016

(54) COLUMN-TYPE SOLID-LIQUID COUNTERCURRENT CONTACT APPARATUS, SOLID PARTICLE WASHING APPARATUS, AND METHOD

(75) Inventors: Tomoyoshi Koizumi, Tokyo (JP); Kimihiko Kikuchi, Tokyo (JP)

(73) Assignee: KUREHA CORPORATION, Tokyo (JP)

( * ) Notice: Subject to any disclaimer, the term of this patent is extended or adjusted under 35 U.S.C. 154(b) by 931 days.

(21) Appl. No.: 13/581,946

(22) PCT Filed: Feb. 23, 2011

(86) PCT No.: PCT/JP2011/053994
§ 371 (c)(1),
(2), (4) Date: Aug. 30, 2012

(87) PCT Pub. No.: WO2011/108420
PCT Pub. Date: Sep. 9, 2011

(65) Prior Publication Data
US 2012/0322972 A1     Dec. 20, 2012

(30) Foreign Application Priority Data

Mar. 1, 2010   (JP) .................................. 2010-044358

(51) Int. Cl.
*B01F 7/16*   (2006.01)
*B01F 7/00*   (2006.01)
(Continued)

(52) U.S. Cl.
CPC .............. *B01F 7/169* (2013.01); *B01F 7/00633* (2013.01); *B01F 7/18* (2013.01); *B01J 8/008* (2013.01); *B01J 8/10* (2013.01); *B01J 8/12* (2013.01); *C07C 319/14* (2013.01); *C08G 75/02* (2013.01); *C08L 71/00* (2013.01); *C08L 81/06* (2013.01); *B01F 2215/0431* (2013.01); *B01J 2208/0084* (2013.01);
(Continued)

(58) Field of Classification Search
None
See application file for complete search history.

(56) References Cited

U.S. PATENT DOCUMENTS 4,750,994 A * 6/1988 Schneider ........... B01F 3/04531
209/169
2006/0254622 A1   11/2006 Fujita et al.
(Continued)

FOREIGN PATENT DOCUMENTS

| JP | 49-41029 B | 11/1974 |
| JP | 54-12265 B | 5/1979 |
| JP | 61-255933 A | 11/1986 |
| JP | 2008-513186 A | 5/2008 |

(Continued)

*Primary Examiner* — Michael Kornakov
*Assistant Examiner* — Ryan Coleman
(74) *Attorney, Agent, or Firm* — Birch, Stewart, Kolasch & Birch, LLP

(57) ABSTRACT

A column-type solid-liquid countercurrent contact apparatus, a washing apparatus for solid particles such as poly(arylene sulfide) (PAS) particles, a PAS manufacturing apparatus, a method of solid-liquid countercurrent contact, a method of washing solid particles such as PAS particles, and a method of manufacturing PAS, wherein a column top part, a column body part, and a column bottom part are included, the column body part is provided with a plurality of stirring chambers connected in the vertical direction and mutually divided by a ring-shaped partitioning plate, a paddle blade (a blade diameter/a diameter of the stirring chamber≥0.65 and the blade diameter/the diameter of the stirring chamber≤0.10) and a baffle are disposed at each of the plurality of stirring chambers, and a disc having a size covering at least a part of a communication opening positioned below the paddle blade is attached to a rotating shaft or to the paddle blade.

16 Claims, 2 Drawing Sheets

(51) Int. Cl.
*B01F 7/18* (2006.01)
*B01J 8/00* (2006.01)
*B01J 8/10* (2006.01)
*B01J 8/12* (2006.01)
*C07C 319/14* (2006.01)
*C08G 75/02* (2016.01)
*C08L 71/00* (2006.01)
*C08L 81/06* (2006.01)

(52) U.S. Cl.
CPC .. *B01J 2208/00867* (2013.01); *C08G 2650/40* (2013.01); *C08L 2205/02* (2013.01)

(56) References Cited

U.S. PATENT DOCUMENTS

2007/0015935 A1    1/2007   Fujita et al.
2008/0025143 A1*   1/2008   Ohashi ............... B01F 13/1016
                                                366/181.4

FOREIGN PATENT DOCUMENTS

| WO | 2005-032736 A1 | 4/2005 |
| WO | 2005-033058 A1 | 4/2005 |
| WO | 2006-030588 A1 | 3/2006 |

* cited by examiner

COLUMN-TYPE SOLID-LIQUID COUNTERCURRENT CONTACT APPARATUS, SOLID PARTICLE WASHING APPARATUS, AND METHOD

TECHNICAL FIELD

The present invention relates to a column-type solid-liquid countercurrent contact apparatus that causes solid particles and a liquid to be subjected to countercurrent contact. More specifically, the present invention relates to the column-type solid-liquid countercurrent contact apparatus including a plurality of stirring chambers, which suppresses a short path of the solid particles as well as stagnation of the solid particles in the vicinity of a wall of the stirring chamber, and moreover, suppresses backward flow of the solid particles to an upper connected stirring chamber, thereby improving contact efficiency between the solid particles and the liquid.

The column-type solid-liquid countercurrent contact apparatus of the present invention can be used for a unit operation mainly in the chemical industry such as washing, purification, extraction, impregnation, chemical reaction, and dissolution of the solid particles since the flow of the solid particles and the flow of the liquid can be continuously subjected to the countercurrent contact for a sufficient time. Therefore, the present invention relates to a washing apparatus that causes the solid particles such as polymer particles like polymerized poly(arylene sulfide) (PAS) particles and a washing liquid to be subjected to the countercurrent contact, and a polymer manufacturing apparatus.

BACKGROUND ART

In a field of the chemical industry, various solid-liquid contact apparatuses are used for performing operation such as washing, purification, extraction, impregnation, chemical reaction, and dissolution of the solid by causing the solid and the liquid to be contacted. As the solid-liquid contact apparatus, a column-type solid-liquid countercurrent contact apparatus (also, referred to as longitudinal solid-liquid countercurrent contact apparatus) is known in which the solid particles and the liquid are continuously subjected to the countercurrent contact as an upward flow and a downward flow, respectively.

The column-type solid-liquid countercurrent contact apparatus has an advantage of having high throughput capability compared to other solid-liquid contact apparatuses because of its high processing power and high contact efficiency between the solid particles and the liquid.

For example, Japanese Patent Publication (JP-B) No. 54-12265 (Patent Literature 1) discloses that an ingredient and a solvent are subjected to the countercurrent contact using a multi-step extraction apparatus that includes an extraction apparatus body, a step partitioning between the steps, a partitioning stirring blade, and a partitioning stirring shaft. WO 2005/33058 A1 (Patent Literature 2, and corresponding to US 2007/0015935 A1 and EP 1669343 A1) discloses a method of manufacturing terephtalic acid in which the countercurrent contact is performed using a column that includes a plurality of stirring blades in the vertical direction.

Also, WO 2005/32736 A1 (Patent Literature 3, and corresponding to US 2006/0254622 A1 and EP 1669140 A1) discloses a method and an apparatus of continuously washing the solid particles in which the solid particles are supplied from an upper part of a longitudinal washing tank to form a high concentration zone of the solid particles in the washing tank, and the high concentration zone is subjected to the countercurrent contact with an upward flow of the washing liquid while being stirred with a plurality of stirring blades.

Further, Japanese Patent Application Laid-Open (JP-A) No. 2008-513186 (Patent Literature 4, and corresponding to WO 2006/030588 A1) proposes a longitudinal solid-liquid countercurrent contact apparatus in which a plurality of stirring chambers mutually divided by a partitioning plate that has a communication opening, and connected in the vertical direction is provided, a radial ejection type stirring blade and one or more baffles fixed to an inner side of a side wall are provided in each stirring chamber, and a solid inlet and a liquid inlet are provided at an upper part and a lower part.

In these conventional column-type solid-liquid countercurrent contact apparatuses, by providing a plurality of stirring blades and divided chambers, the solid-liquid contact is sufficiently performed while the solid particles move in the longitudinal direction. The column-type solid-liquid countercurrent contact apparatus is expected to have high processing power, and moreover, to perform highly-efficient and uniform contact with a small amount of the solid-liquid contact. To enhance the contact efficiency in the solid-liquid countercurrent contact apparatus, it is necessary to continuously and rapidly renew a contact interface between the solid particles and the liquid.

Therefore, the conventional column-type solid-liquid countercurrent contact apparatus is provided with a plurality of divided chambers connected in the longitudinal direction via a communication opening, and a stirring blade is provided in each divided chamber. The contact interface between the solid particles and the liquid is continuously and rapidly renewed by stirring with the stirring blade. Accordingly, the solid particles after the contact process are moved and settled in the next divided chamber by an action of gravity, and the contact process with a new liquid flowing upward is performed. The above processes are repeated.

However, the contact efficiency between the solid particles and the liquid has not yet been sufficient. That is, in the divided chamber provided with a stirring blade (hereinafter, referred to as "stirring chamber"), the following phenomena might happen: a renewal speed of the contact interface between the solid particles and the liquid becomes non-uniform, backmixing occurs in which the solid particles after contact process in the stirring chamber is again in contact with the liquid with which the contact process has been already performed instead of a new liquid, non-uniformity occurs in moving time of the solid particles settling from one stirring chamber to a lower connected stirring chamber, and in some cases, the solid particles after being subjected to the contact process in the stirring chamber pass through the communication opening by accompanying the upward flow of the liquid, and flow backward to an upper connected stirring chamber.

If these phenomena occur, not only is the processing efficiency of the column-type solid-liquid countercurrent contact apparatus lowered, but also the time of being subjected to the solid-liquid countercurrent contact per solid particle differs, whereby uniformity of quality of the solid particles which are subjected to the solid-liquid countercurrent contact process and recovered as products is lost. Therefore, improvement of the apparatus has been sought.

As the stirring blade used in the solid-liquid countercurrent contact apparatus, a paddle blade such as a flat paddle blade, an inclined paddle blade, a V-type paddle blade, a pfaudler blade, or a brumargin blade, a turbine blade such as a turbine blade or a fan turbine blade, and a propeller blade such as a marine propeller blade are known. Among these blades, it is known that the paddle blade and the turbine blade are more likely to generate mainly the flow in a blade radial direction by a centrifugal action of blade rotations, whilst the propeller blade is more likely to generate the flow in an axial direction by thrust in the direction of the rotating shaft. It is also known that, in both cases, the direction of the flow to be generated is adjustable to some extent by changing a shape, an attaching angle of the blade, or the like.

The stirring blade provided in the stirring chamber of the column-type solid-liquid countercurrent contact apparatus is required to cause the solid particles to stay in the stirring chamber for a predetermined time, and to be subjected to the solid-liquid contact. When the propeller blade is used as the stirring blade, which generates the flow mainly in the axial direction, the solid particles supplied from above are more likely to be discharged from the stirring chamber in a relatively short time due to the downward flow of the axial direction. In contrast, when the paddle blade or the turbine blade is used, the flow rotating in the stirring chamber can cause the solid particles to stay in the stirring chamber for a relatively long time.

The solid particles subjected to the solid-liquid contact in the stirring chamber are gradually settled by an action of gravity, and are discharged to a lower connected stirring chamber through the communication opening. A staying time of the solid particles in the stirring chamber is adjustable by changing a shape of a blade, an attaching angle, and a rotation speed of the paddle blade or of the turbine blade.

Therefore, the paddle blade or the turbine blade is preferably used as the stirring blade provided in the stirring chamber of the column-type solid-liquid countercurrent contact apparatus. Among these blades, the paddle blade is widely employed because of its simple structure, low manufacturing cost, and low maintenance cost, wherein the paddle blade is formed of an approximately planar vane plate that is radially provided to a rotating shaft in a protruding manner.

However, when the paddle blade is employed as the stirring blade provided in the stirring chamber of the column-type solid-liquid countercurrent contact apparatus, the above-described inconvenient phenomena occur relatively remarkably, the inconvenient phenomena being such that not only is the processing efficiency of the column-type solid-liquid countercurrent contact apparatus lowered, but also the time of being subjected to the solid-liquid countercurrent contact per solid particle differs, whereby uniformity of quality of the solid particles which are subjected to the solid-liquid countercurrent contact process and recovered as products is lost. Therefore, improvement has been strongly sought. Improvement can be achieved to some extent by decreasing a flow rate of the solid particles and the liquid, or by decreasing the cross-sectional area of the communication opening of each stirring chamber in the horizontal direction. However, as a result, the processing power is significantly decreased.

The inventors diligently proceeded with a study on generation mechanism of the above-described inconvenient phenomena that occur when the paddle blade is employed as the stirring blade provided in the stirring chamber of the column-type solid-liquid countercurrent contact apparatus. As a result, it has been found out that occurrence of a short path is the major reason, where the solid particles in the vicinity of the rotating shaft, to which the paddle blade is fixed, are discharged from the stirring chamber without being subjected to the solid-liquid countercurrent contact in the stirring chamber for a sufficient time.

The paddle blade is a stirring blade wherein typically two to eight approximately planar vane plates are radially provided to the rotating shaft at even intervals in a protruding manner, and causes the liquid to flow mainly in a radial direction by rotating the rotating shaft in the liquid. Especially, the flat paddle blade causes the flow mostly in the radial direction wherein a planar vane plate is provided parallel to the axial direction of the rotating shaft in a protruding manner. However, in a case of the inclined paddle blade, the proportions of the flows generated in the radial and axial directions are changed depending on an inclined angle. Also, in a case of the pfaudler blade, the proportion of the flow in the axial direction is large. That is, in the case of the paddle blade, the ratio between the flows in the radial and axial directions caused in the stirring chamber is adjustable by changing the shape, the size, the attaching angle of the vane plate, and the like.

The rotation of the paddle blade causes the flow of the liquid in the stirring chamber mainly in the radial direction, whereby the solid particles are not discharged from the stirring chamber in a short time, and the solid particles and the liquid can contact each other while staying in the stirring chamber and renewing the contact interface.

In a case where the density of the solid particles is larger than that of the liquid, the solid particles are gradually settled in the liquid by an action of gravity. In the stirring chamber, typically, about two to eight baffles, which extend in the vertical direction along an inner wall surface, are provided in the radial direction at even intervals in a protruding manner, whereby the flow of the liquid being stirred up and down can be caused as well as the flow in the radial or circumferential direction. Therefore, the settlement of the solid particles is alleviated. Also, by disposing the baffle, a hindrance to the renewal of the contact interface due to corotation of the solid particles and the liquid can be prevented.

In this way, for a given length of time, the solid particles are gradually settled in the stirring chamber while being subjected to the solid-liquid contact process, and pass through the communication opening to be discharged into a lower connected stirring chamber. Thus, the solid particles gradually flow downward whilst the liquid flows upward so that the solid-liquid countercurrent contact is performed in the apparatus.

The paddle blade is formed of an approximately planar vane plate being radially provided to the rotating shaft at even intervals in a protruding manner, and a turning angle velocity of the vane plate is increased in proportion to the distance from the rotating shaft. Meanwhile, the turning angle velocity of the approximately planar vane plate is small in the vicinity of the rotating shaft. Therefore, the flow of the liquid in the radial and circumferential directions becomes small, and the movement of the solid particles in the radial and circumferential directions becomes small. Further, in the vicinity of the rotating shaft, the influence of the flow being stirred up and down is small, where the flow is caused by the baffle provided on the inner wall surface of the column body part. The solid particles in the vicinity of the rotating shaft are gradually settled in the stirring chamber by an action of gravity under the condition of the solid particles being less likely to be influenced by the flow of the liquid being stirred up and down or by the flow of the liquid in the radial and circumferential directions. As a result, the solid particles in the vicinity of the rotating shaft are, without being subjected to the solid-liquid countercurrent contact for a sufficient time, more likely to pass through the communication opening along the axial direction of the rotating shaft in the stirring chamber and to be discharged into the lower connected stirring chamber in a relatively short time. Therefore, the solid particles discharged into a lower connected stirring chamber have a high probability of existing in the vicinity of the rotating shaft. Therefore, again, in the stirring chamber, the solid particles are, without being subjected to the solid-liquid countercurrent contact for a sufficient time, more likely to pass through the communication opening along the axial direction of the rotating shaft and to be discharged into a further lower connected stirring chamber in a relatively short time.

The inventors of the present invention have found out, in the column-type solid-liquid countercurrent contact apparatus, that the short path (S in FIG. 3) occurs wherein the solid particles are discharged from the apparatus without being substantially subjected to the solid-liquid countercurrent contact.

Further, the solid particles without being subjected to the solid-liquid countercurrent contact for a sufficient time increase due to the occurrence of the short path. Therefore, the inconvenience is caused wherein the processing efficiency of the column-type solid-liquid countercurrent contact apparatus is decreased, and the uniformity of quality of the solid particles recovered as a product is lost.

Meanwhile, to enhance the solid-liquid countercurrent contact efficiency, it is effective to increase the number of stirring rotations to facilitate the solid-liquid contact. However, as a result, the stirring power is increased, and up and down movement of the solid particles is facilitated. Accordingly, the solid particles flow back to an upper connected stirring chamber, and the uniformity of the solid-liquid countercurrent contact is impaired. Therefore, if the number of stirring rotations is increased too much, the contact efficiency is decreased accordingly. Furthermore, the number of stirring rotations at a low speed causes stagnation/settlement of the solid particles in the vicinity of a wall of the stirring chamber, whereby the effective volume of the stirring chamber as a space for the solid-liquid contact is decreased, and contact time of the solid and the liquid is decreased.

CITATION LIST

Patent Literature

Patent Literature 1: JP-B 54-12265
Patent Literature 2: WO 2005/33058 A1
Patent Literature 3: WO 2005/32736 A1
Patent Literature 4: JP-A 2008-513186 (through PCT route)

SUMMARY OF INVENTION

Technical Problem

The present invention provides a column-type solid-liquid countercurrent contact apparatus which includes a column top part, a column body part, and a column bottom part. The column body part is provided with a plurality of stirring chambers mutually divided by each ring-shaped partitioning plate having a communication opening in the center thereof, and connected in the vertical direction. Each of the plurality of stirring chambers includes a paddle blade fixed to a shared rotating shaft which passes through the communication opening of each ring-shaped partitioning plate, and at least one baffle extending in the vertical direction along an inner wall surface of the column body part. An object of the present invention is to improve the column-type solid-liquid countercurrent contact apparatus, wherein the occurrence of the short path is effectively prevented in which a part of the solid particles is discharged from the stirring chamber and from the column-type solid-liquid countercurrent contact apparatus in a short time without being subjected to sufficient solid-liquid countercurrent contact in the stirring chamber. Further, flowing back of the solid particles into an upper connected stirring chamber is suppressed while the solid-liquid countercurrent contact is facilitated by stirring. Furthermore, decrease of an effective volume of the stirring chamber due to stagnation/settlement of the solid particles in the vicinity of a wall of the stirring chamber is suppressed.

Solution to Problem

The inventors of the present invention diligently studied the solution to the above-described problem. As a result, it has been found out that the column-type solid-liquid countercurrent contact apparatus having the following structure suppresses the short path of the solid particles and the stagnation of the solid particles in the vicinity of the wall of the stirring chamber, whereby the contact efficiency between the solid particles and the liquid can be improved. The column-type solid-liquid countercurrent contact apparatus includes a column body part, wherein a paddle blade having a specific blade diameter and blade width is disposed at a plurality of stirring chambers mutually divided by each ring-shaped partitioning plate having a communication opening in the center thereof and connected in the vertical direction, and a disc adjacent to the paddle blade and having a size of covering at least one part of the communication opening positioned below the paddle blade is attached to the rotating shaft or to the paddle blade so as not to have a gap between the circumference of the rotating shaft and the disc.

The present invention provides a column-type solid-liquid countercurrent contact apparatus including a column top part, a column body part, and a column bottom part, for causing solid particles and a liquid to be subjected to countercurrent contact, the column body part including: a plurality of stirring chambers connected in a vertical direction and mutually divided by each of ring-shaped partitioning plates having a communication opening in the center thereof, each of the plurality of stirring chambers including: a paddle blade fixed to a shared rotating shaft passing through the communication opening of each of the ring-shaped partitioning plates, and satisfying the following formulas (1) and (2):

$$\text{(a blade diameter of the paddle blade)/(a diameter of the stirring chamber)} \geq 0.65 \quad \text{formula (1)}$$

$$\text{(a blade width of the paddle blade)/(the diameter of the stirring chamber)} \leq 0.10 \quad \text{formula (2);}$$

at least one baffle extending in the vertical direction along an inner wall surface of the column body part; and a disc having a size covering at least a part of the communication opening positioned below the paddle blade being adjacent to the paddle blade, and being attached to the rotating shaft or to the paddle blade so as not to have a gap between a circumference of the rotating shaft and the disc.

The present invention also provides the column-type solid-liquid countercurrent contact apparatus, wherein (a) the column top part includes a solid particle inlet through which the solid particles or a slurry containing the solid particles are supplied, (b) the column top part includes, at an upper part than the solid particle inlet, a liquid outlet through which the liquid is discharged, (c) the column bottom part includes a liquid inlet through which a liquid for contact with the solid particles is supplied, and (d) the column bottom part includes, at a lower part than the liquid inlet, a processed product outlet through which a processed product is removed, the processed product resulting from the solid particles being subjected to contact process with the liquid for contact.

The present invention also provides the column-type solid-liquid countercurrent contact apparatus, wherein the paddle blade is a flat paddle blade.

The present invention also provides the column-type solid-liquid countercurrent contact apparatus, wherein the paddle blade is disposed at a lower half region of each of the stirring chambers.

The present invention also provides the column-type solid-liquid countercurrent contact apparatus, wherein a ratio of an area of the communication opening of each of the ring-shaped partitioning plates in a horizontal direction to a cross-sectional area of each of the stirring chambers in the horizontal direction is within a range of 4 to 25%.

The present invention also provides the column-type solid-liquid countercurrent contact apparatus, wherein the communication opening has a circular shape.

The present invention also provides the column-type solid-liquid countercurrent contact apparatus, wherein a diameter of the disc having a circular shape is larger than that of the rotating shaft and has a ratio within a range of 0.3 to 1.2 times the diameter of the communication opening of each of the ring-shaped partitioning plates.

The present invention also provides the column-type solid-liquid countercurrent contact apparatus, wherein a ratio H/D between a height H and an inner diameter D of each of the stirring chambers is within a range of 0.2 to 3.0.

The present invention also provides the column-type solid-liquid countercurrent contact apparatus, wherein the solid particles are PAS particles.

The present invention also provides a solid particle washing apparatus, particularly a PAS particle washing apparatus, including the column-type solid-liquid countercurrent contact apparatus.

The present invention also provides a PAS manufacturing apparatus including the column-type solid-liquid countercurrent contact apparatus.

Further, according to the present invention, a method of solid-liquid countercurrent contact, especially, a method of solid-liquid countercurrent contact of PAS particles, and a method of manufacturing PAS using the above-described column-type solid-liquid countercurrent contact apparatus are provided.

Further, according to the present invention, a method of washing solid particles, especially, washing PAS particles using the above-described washing apparatus is provided.

Advantageous Effects of Invention

The column-type solid-liquid countercurrent contact apparatus of the present invention suppresses a short path of the solid particles having mainly a large particle diameter in the vicinity of the stirring shaft, so that a contact time between the solid particles and the liquid can be increased. Moreover, stagnation of the solid particles in the vicinity of the stirring chamber is suppressed, so that an effective volume of the stirring chamber can be secured. Furthermore, mixture of the solid particles in the up and down direction is suppressed, so that the frequency of going in and out of the upper stirring chamber by the solid particles can be decreased. As a result, the column-type solid-liquid countercurrent contact apparatus and the method of the solid-liquid countercurrent contact of the present invention have an effect of improving contact efficiency between the solid particles and the liquid. Therefore, the column-type solid-liquid countercurrent contact apparatus and the method of solid-liquid countercurrent contact of the present invention have an effect of being effectively used for a unit operation mainly in the chemical industry such as washing, purification, extraction, impregnation, chemical reaction, and dissolution of the solid particles with the high contact efficiency between the solid particles and the liquid. Especially, when it is used for washing the solid particles, high washing efficiency can be obtained. Therefore, there is an effect of being effectively used for washing the solid particles such as PAS particles, or for manufacturing PAS.

DESCRIPTION OF EMBODIMENTS

Figure 1:
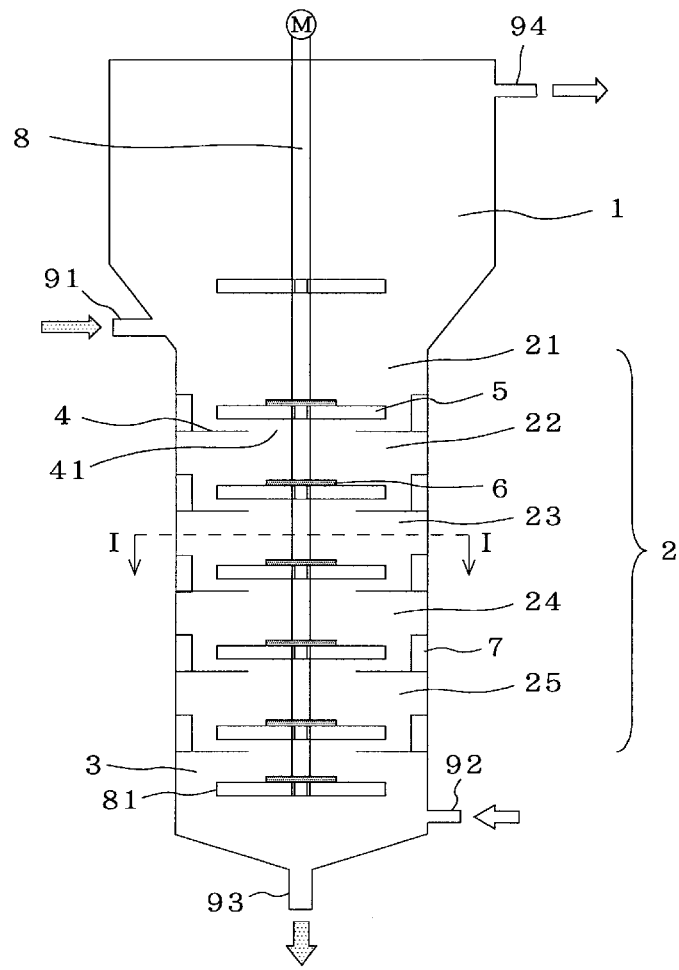
FIG. 1 is a schematic longitudinal sectional view of an example of a column-type solid-liquid countercurrent contact apparatus according to the present invention in which an improved paddle blade is disposed.

Referring to FIG. 1, a column-type solid-liquid countercurrent contact apparatus of the present invention includes a column top part 1, a column body part 2, and a column bottom part 3.

[Stirring Chamber]

A plurality of stirring chambers is disposed at the column body part 2 which is positioned between the column top part 1 and the column bottom part 3. A plurality of stirring chambers is mutually divided by a ring-shaped partitioning plate 4 having a communication opening 41 in the center thereof, and is connected in the vertical direction. The number of the stirring chambers can be properly selected in accordance with an inner diameter or a height of the column body part, and is changeable within a range of 2 to 100 in accordance with the number of necessary theoretical solid-liquid contact steps. The number of the stirring chambers is preferably 3 to 50, and particularly preferably 4 to 20. In an example of FIG. 1, the stirring chambers are divided into five stirring chambers 21 to 25. Each of the stirring chambers has substantially a cylindrical shape, and a ratio H/D between a height H and an inner diameter D of the stirring chamber is typically 0.1 to 4.0, preferably 0.2 to 3.0, and particularly preferably 0.3 to 2.0. In a case where a solid-liquid density ratio, that is, (density of a solid)/(density of a liquid) is large, it is preferable to make H/D large, whereas in a case where the solid-liquid density ratio is small, H/D can be made small, whereby the overall height of the column-type solid-liquid countercurrent contact apparatus can be decreased.

A paddle blade and at least one baffle that extends in the vertical direction along an inner wall surface of the column body part 2 are arranged in each of the stirring chambers 21 to 25. Each paddle blade is fixed to a stirring shaft 8 as a shared rotating shaft that passes through the communication openings 41 of the ring-shaped partitioning plates 4.

[Communication Opening]

The communication opening 41 of the ring-shaped partitioning plate 4 has no limitation on shape and size as long as it enables the upper and lower stirring chambers to communicate each other. However, if the communication opening has a square portion, solid particles can be deposited on the square portion, or flow of the solid particles or a liquid can be disrupted. Therefore, the communication opening 41 preferably has a circular shape. A ratio of an area of the communication opening in the horizontal direction to a cross-sectional area of the stirring chamber in the horizontal direction is 1 to 36%, and preferably 4 to 25%. Therefore, when the communication opening has a circular shape, the ratio of the diameter of the communication opening to the diameter of the ring-shaped partitioning plate (that is the same as the inner diameter D of the stirring chamber) is typically 0.1 to 0.6, and preferably 0.2 to 0.5. If the communication opening is too large, the solid particles are discharged into a directly lower stirring chamber without being subjected to sufficient solid-liquid countercurrent contact in each stirring chamber. Therefore, due to this repetition, the solid-liquid countercurrent contact in the column-type solid-liquid countercurrent contact apparatus becomes insufficient. On the other hand, if the communication opening is too small, the solid particles subjected to the sufficient solid-liquid countercurrent contact in each stirring chamber cannot be discharged into the directly lower stirring chamber, and a contact with a new liquid cannot be performed. As a result, the solid-liquid countercurrent contact in the column-type solid-liquid countercurrent contact apparatus becomes insufficient, and processing time becomes extremely long, whereby processing efficiency becomes lowered. Adjacent stirring chambers are connected by an opening having an area in the horizontal direction obtained by subtracting the cross-sectional area of the stirring shaft 8 in the horizontal direction from the area of the communication opening 41 in the horizontal direction. Therefore, the area of the communication opening 41 in the horizontal direction is selected in consideration of the cross-sectional area of the stirring shaft 8 in the horizontal direction. The shape and the area in the horizontal direction of each of the communication openings 41 may be the same, or may be different. For example, the areas of the communication openings in the horizontal direction may be gradually decreased from an upper communication opening to a lower communication opening.

[Paddle Blade]

Examples of the paddle blade include a flat paddle blade, a V-type paddle blade, a pfaudler blade, an inclined paddle blade, and a brumargin blade. However, the flat paddle blade that substantially causes only the flow of a liquid in a radial direction is particularly preferable. Therefore, the following description will be given by taking a flat paddle blade 5 as an example. In a case where other paddle blades are employed, it is necessary to cause the liquid flow mainly in a radial direction, and is also necessary to employ a blade having a shape not to cause the salient liquid flow in an axial direction. Some of the paddle blades disposed in each stirring chamber may be paddle blades other than the flat paddle blade. However, it is preferable to employ the flat paddle blade 5 for all the paddle blades so that stirring efficiency can be enhanced. The number of vane plates of the paddle blade is typically two to six, and four vane plates are particularly preferable because of a good balance.

A blade diameter d of the paddle blade needs to satisfy (the blade diameter d of the paddle blade)/(the diameter D of the stirring chamber)≥0.65, preferably d/D≥0.70, and more preferably d/D≥0.73, so that the contact efficiency can be increased. Although there is no upper limit for d/D, it is typically 0.90 or less, preferably 0.85 or less, and particularly preferably 0.80 or less. If d/D is too small, the solid particles are stagnated in the vicinity of a wall of the stirring chamber, and an effective volume of the stirring chamber becomes decreased, whereby efficiency of the solid-liquid countercurrent contact is deteriorated. In the present invention, the blade diameter of the paddle blade is represented by a total of the lengths of two paddle blades and the outer diameter of the stirring shaft.

Also, a blade width h of the paddle blade needs to satisfy (the blade width h of the paddle blade)/(the diameter D of the stirring chamber)≤0.10, preferably h/D≤0.08, and more preferably h/D≤0.06. Although there is no lower limit for h/D, it is typically 0.01 or more, preferably 0.012 or more, and more preferably 0.015 or more in order to retain the strength of the paddle blade. If h/D is too large, mixture of the solid particles in the up and down direction is caused, and the frequency of going in and out between the stirring chambers by the solid particles is increased, whereby the contact efficiency between the solid particles and the liquid is decreased.

Note that, typically, a turbine blade or a propeller blade is also known as the stirring blade disposed in the stirring chamber. However, since the propeller blade causes the liquid flow in the axial direction, and the turbine blade has a high cutting effect, neither of them can perform sufficient solid-liquid countercurrent contact in the stirring chamber. Therefore, they are not preferable in the present invention.

Each of the paddle blades 5 disposed in each stirring chamber is disposed above the communication opening of each ring-shaped partitioning plate so that sufficient solid-liquid countercurrent contact can be performed in the stirring chamber, and is preferably disposed at a lower half region of the stirring chamber so that the solid particles can stay in the stirring chamber for a predetermined time and unintended discharging of the solid particles can be prevented.

[Baffle]

A baffle 7 disposed in each stirring chamber is a planar member extending in the vertical direction along an inner wall surface of the column body part. Existence of the baffle 7 can cause the flow of the liquid to be stirred up and down as well as the flow in the radial or circumferential direction. Therefore, the settlement of the solid particles is alleviated. Further, by disposing the baffle, a hindrance to the renewal of the contact interface can be prevented, which may occur due to corotation of the solid particles and the liquid in accordance with the rotation of the paddle blade 5. As the baffle 7 disposed in each stirring chamber, two to eight baffles may be disposed at equal intervals in the circumferential direction. In the illustrated example, four baffles 7 are disposed. A height in the vertical direction, a protruding height in the radial direction, and a fixing position of the baffle 7 can be determined in accordance with the height H and the inner diameter D of each stirring chamber, the shape and the size of the paddle blade, a feeding speed of a solid (slurry) and a feeding speed of the liquid, or the like. The baffle 7 disposed in each stirring chamber is preferably disposed to be biased into a lower side of each stirring chamber, that is, to be arranged at a position fallen within the lower half region of each stirring chamber so that sufficient solid-liquid countercurrent contact can be performed in each stirring chamber. The baffle 7 may be directly fixed to the ring-shaped partitioning plate, and the distance between the baffle 7 and the ring-shaped partitioning plate may be zero.

[Rotating Shaft]

The stirring shaft 8 as a rotating shaft, to which each of the paddle blades 5 is fixed, is a shared rotating shaft that passes through the communication openings 41 of the ring-shaped partitioning plates 4 as well as the column top part 1 and the column body part 2. As described above, the adjacent stirring chambers are connected by the opening having the area in the horizontal direction obtained by subtracting the cross-sectional area of the stirring shaft 8 in the horizontal direction from the area of the communication opening 41 in the horizontal direction. It is apparent that the diameter of the stirring shaft 8 is smaller than the communication opening 41. However, if the diameter of the stirring shaft 8 is too small, the strength of the stirring shaft 8 itself is lowered, and the area of the opening in the horizontal direction is increased. As a result, a short path of the solid particles may occur without being subjected to sufficient solid-liquid contact in the stirring chamber. Therefore, the diameter of the stirring shaft 8 may be a size in the range of 5 to 35% of the diameter of the communication opening 41, preferably 10 to 30%, and particularly preferably 12 to 25%.

The paddle blade 5 is attached and fixed to the stirring shaft 8 as the rotating shaft at a position in each stirring chamber of the column body part 2. Although the stirring shaft 8 may have a length ending in the column body part 2, the length preferably extends into the column bottom part 3 so that the stirring efficiency of the entire column-type solid-liquid countercurrent contact apparatus can be enhanced. In a case where a tip of the stirring shaft 8 is positioned in the column bottom part 3, the stirring blade is preferably attached to the tip of the stirring shaft 8. It is preferable to attach the stirring blade to the tip, so that the solid-liquid contact can be performed in the column bottom part 3 in a similar manner to each stirring chamber, and countercurrent contact efficiency of the column-type solid-liquid countercurrent contact apparatus can be increased.

The stirring shaft 8 as the rotating shaft is rotationally driven by a motor provided above the column top part of the solid-liquid countercurrent contact apparatus. Although the number of rotations of the stirring shaft can be properly determined within a range where the solid particles and the liquid can be sufficiently in contact with each other in each stirring chamber, stirring power per unit volume (Pv) may be determined to be 0.1 to 35 $W/m^3$, preferably 0.3 to 20 $W/m^3$, and more preferably 0.5 to 10 $W/m^3$. As the number of rotations corresponding to the above Pvs, a so-called low-speed rotation range of approximately 5 to 100 rpm, preferably 8 to 60 rpm, more preferably 9 to 50 rpm, and particularly preferably 10 to 40 rpm can be adopted. If the number of rotations of the stirring shaft is too large, up and down movement of the solid particles is facilitated, the solid particles flow back to the upper connected stirring chamber, and uniformity of the solid-liquid countercurrent contact is deteriorated, whereby the contact efficiency is decreased. Therefore, as a result of insufficient performance of processes such as chemical reaction and washing, the processing efficiency is lowered. If the number of rotations of the stirring shaft is too small, the liquid that has contacted the solid particles maintains corotation for a long time. Accordingly, the solid particles cannot be in contact with a new liquid, whereby the processing efficiency is also lowered.

[Disc]

The column-type solid-liquid countercurrent contact apparatus of the present invention includes a disc 6 which is adjacent to the paddle blade 5, and covering at least a part of the communication opening 41 positioned below the paddle blade 5. The disc 6 is fixed to the rotating shaft or to the paddle blade so as not to have a gap between the disc 6 and an outer circumference of the rotating shaft. The disc 6 may be disposed adjacent to all of the paddle blades 5 which are disposed in each stirring chamber, or may not be disposed in a part of the paddle blades 5. However, the disc 6 is disposed in at least over half of the paddle blades 5.

The disc 6 has a size of covering at least a part of the communication opening 41 positioned below the paddle blade 5, and has a shape capable of being attached and fixed to the stirring shaft 8 or to the paddle blade 5 so as not to have a gap between the circumference of the stirring shaft 8 and the disc 6 around the stirring shaft 8 as the rotating shaft. The disc 6 has typically a circular shape or an oval shape, and the circular shape is preferable so as not to cause deposition of the solid particles or not to induce an unexpected flow of the solid particles. Although each disc has typically a solid planar shape, a portion apart from the center of the disc may employ mesh.

Although all of the discs may have the solid planar shape, a part of the discs may have the oval shape, and a part of the discs may have a mesh portion that is apart from the center of the disc.

The disc 6 is adjacent to the paddle blade 5, and is attached and fixed to the stirring shaft 8 or to the paddle blade 5 so as not to have a gap between the circumference of the stirring shaft 8 and the disc 6. For example, the disc may be formed by assembling two to four fan-shaped parts around the stirring shaft 8. The fan-shaped parts are obtained in such a way that a doughnut-shaped disc having a void in its center which has the same diameter as the stirring shaft 8 is divided into two to four pieces in the circumferential direction. The disc may then be attached and fixed to the stirring shaft 8 or to the paddle blade 5 so as not to have a gap between the circumference of the stirring shaft 8 and the disc 6. Each of the discs 6 may be adjacently attached to only one of above or below the paddle blade 5, or may be adjacently attached to both of above and below the paddle blade 5. When the disc 6 is attached below the paddle blade 5, the solid particles can be deposited. Therefore, it is preferable to adjacently attach the disc 6 above the paddle blade 5. Each of the discs 6 may just be adjacent to the paddle blade 5. Each of the discs 6 may be directly in contact with and attached to the paddle blade 5, or may be attached slightly above or below the paddle blade 5 with a small distance therebetween. The attachment of the disc 6 to the stirring shaft 8 or to the paddle blade 5 may be performed by directly attaching and fixing the disc 6 to the stirring shaft 8 or to the paddle blade 5 with a bolt or the like. Fixtures having various shapes can be used in order to alleviate deformation of the disc 6, and to ensure the attachment of the disc 6 to the stirring shaft 8 or to the paddle blade 5.

The disc 6 made of metal such as stainless steel or of rigid resin can be used. When the fixture is used, a disc made of rigid resin such as acrylic resin or polycarbonate resin can be used as the disc 6.

The disc 6 may have a lager diameter than the stirring shaft 8, and may have a size covering at least a part of the communication opening 41 positioned below each of the paddle blades 5. In a case where the disc 6 and the communication opening 41 have circular shapes, the diameter of the disc 6 is larger than that of the stirring shaft 8, and typically may have a ratio in the range of 0.2 to 1.5 times the diameter of the communication opening of each ring-shaped partitioning plate, and preferably the ratio in the range of 0.3 to 1.2 times. If the diameter of the disc 6 is too small, only the solid particles very close to the stirring shaft 8 can be prevented from discharging into a lower connected stirring chamber via the communication opening 41 in the axial direction of the stirring shaft 8. Therefore, the occurrence of the short path of the solid particles cannot be suppressed. If the diameter of the disc 6 is too large, the solid particles are not promptly discharged into a directly lower stirring chamber after sufficient solid-liquid contact is performed in the stirring chamber, and the contact with a new liquid is not performed. As a result, the solid-liquid countercurrent contact in the column-type solid-liquid countercurrent contact apparatus becomes insufficient, and the processing time becomes extremely longer, whereby the processing efficiency becomes lowered. When the disc 6 has an oval shape, the longer diameter and the shorter diameter may be selected in accordance with the cross-sectional ratio in the horizontal direction according to the case of the circular shape. The thickness of the disc 6 has no limitation as long as the disc 6 is not easily deformed in accordance to the rotation of the stirring shaft 8. In a case where the disc 6 is made of rigid resin such as acrylic resin or polycarbonate resin, the thickness is typically 0.5 to 3.0 mm, and preferably 1.0 to 2.5 mm. In a case where the disc 6 is made of metal, the thickness is typically 0.2 to 2.5 mm, and preferably 0.5 to 2.2 mm.

[Column Top Part and Column Bottom Part]

The column top part 1 is provided with a solid particle inlet 91, and a liquid outlet 94 positioned above the solid particle inlet 91. The column bottom part 3 is provided with a liquid inlet 92, and a processed product outlet 93 positioned below the liquid inlet 92.

The column top part 1 has a cross-sectional area in the horizontal direction enlarged about 1 to 4 times the column body part 2, as necessary, and is connected to the column body part 2 via a tapered part so that a solid (slurry) introduced through the solid particle inlet 91 is less likely to be subjected to backmixing in the axial direction due to the liquid flow discharged from the liquid outlet 94. Although it is not necessary to dispose a stirring blade at the stirring shaft 8 in the column top part 1, a propeller blade or the like that causes the flow mainly in the axial direction may be disposed so that flowing of the solid (slurry) can be facilitated, the solid being introduced through the solid particle inlet 91 into the stirring chamber 21 provided below the solid particle inlet 91.

The shape of the column bottom part 3 may be an approximately cylindrical shape, and may alternatively be a shape in which the diameter is gradually decreased toward the processed product outlet 93 in a tapered manner. As described above, the tip of the stirring shaft 8 may protrude into the column bottom part 3, or may not protrude. Also, in a case where the tip of the stirring shaft 8 is in the column bottom part, it is not necessary to dispose the stirring blade at the tip of the stirring shaft 8. However, it is preferable to dispose the stirring blade.

[Solid-Liquid Countercurrent Contact Process]

In the apparatus having such a configuration, the solid (slurry) introduced through the solid particle inlet 91 into the column top part 1 is introduced into the first stirring chamber 21 without being subjected to substantial backmixing. The solid (slurry) moves in the radial and circumferential directions, accompanying the liquid flow in the radial direction caused by the rotation of the paddle blade 5 disposed in the stirring chamber 21, and is divided by an action of the baffle 7 fixed to an inner wall of the stirring chamber 21 to move into an upper side and a lower side of an attaching position of the paddle blade 5. The flow principally involving the solid (slurry) stays in the stirring chamber for a predetermined time by forming a circulating flow at the upper side and the lower side of the paddle blade 5, whereby the solid-liquid contact between the solid (slurry) and the liquid introduced through the liquid inlet 92 can be effectively achieved in the stirring chamber 21.

Since the solid particles are gradually settled by an action of gravity, the flow rich in the solid particles passes through the communication opening 41 from the stirring chamber 21, and is introduced into the stirring chamber 22. In the stirring chamber 22, the solid particles are subjected to effective solid-liquid contact with the liquid introduced through the liquid inlet 92, in a similar manner to the stirring chamber 21, under a stirring action of the baffle 7 and the paddle blade 5 provided in the stirring chamber 22.

Further, similar solid-liquid contact process is repeated in the stirring chambers 23 to 25. High solid-liquid contact efficiency of the entire column-type solid-liquid countercurrent contact apparatus is achieved by the repetition of the effective solid-liquid contact process.

The column-type solid-liquid countercurrent contact apparatus of the present invention, as described above, uses a difference in density between solid and liquid. Therefore, the difference in density between the solid and the liquid in the stirring tank (chamber) is necessary. In that sense, the solid-liquid density ratio, that is, (density of the solid)/(density of the liquid) is 1.03 to 20.0, preferably 1.05 to 10.0, and more preferably 1.07 to 5.0. In a case where the solid-liquid density ratio is lower than 1.03, separation of the solid and the liquid results in poor outcome, whilst in a case where the solid-liquid density ratio exceeds 20.0, the solid-liquid contact efficiency is lowered.

The solid (slurry) having been subjected to the solid-liquid contact in the column body part 2 is then, as desired, brought into contact with the liquid introduced through the liquid inlet 92 by the rotation of the stirring blade 81 in the column bottom part 3, and is finally discharged through the processed product outlet 93 as the solid (slurry).

Meanwhile, the liquid introduced through the liquid inlet 92 is subjected to gentle solid-liquid contact in the column bottom part 3, solid-liquid contact along with stirring in the column body part 2, and gentle solid-liquid contact in the column top part 1, with the solid (slurry) introduced through the solid particle inlet 91, and is then discharged through the liquid outlet 94 of the column top part 1.

Note that the whole or a part of the column body part 2 may be formed of a transparent material such as acrylic resin or the like so that the flow of the liquid or the solid particles in each of the stirring chambers 21 to 25 can be observed and confirmed from outside.

The column-type solid-liquid countercurrent contact apparatus of FIG. 1 is applicable to an arbitrary unit operation in which the solid (slurry) is introduced through the solid particle inlet 91, the liquid is introduced through the liquid inlet 92, and the solid-liquid contact is performed in the apparatus. Concrete examples of the unit operation include washing, purification, extraction, impregnation, reaction, and dissolution.

A preferable example of use of the column-type solid-liquid countercurrent contact apparatus of the present invention includes a washing apparatus that performs washing of PAS particles separated and recovered from a PAS slurry, or washing of the PAS particles for purification thereafter.

For example, JP-A 61-255933 discloses a method of processing a polymer slurry containing the PAS particles obtained in a polymerization process. In this processing method, the following processes are described: (1) a process of separating a polymer slurry into PAS particles and a slurry containing a crystalline alkali chloride by screening, the polymer slurry containing the PAS particles, a crystalline and a dissolved alkali chloride as a by-product, an arylene sulfide oligomer, and N-methylpyrrolidone as the main fluid component, (2) a process of obtaining the crystalline alkali chloride by allowing the slurry containing the crystalline alkali chloride to be subjected to solid-liquid separation as well as recovering N-methylpyrrolidone by distilling a fluid component, (3) a process of washing the PAS particles with an organic solvent such as acetone, and water, and (4) a process of distilling and recovering a solvent from an organic solvent washing liquid. The column-type solid-liquid countercurrent contact apparatus of the present invention can be preferably used as a continuous washing apparatus for the above-described process (3).

Therefore, the column-type solid-liquid countercurrent contact apparatus of the present invention can be used as a PAS manufacturing apparatus.

EXAMPLES

Hereinafter, the present invention will be described more concretely with reference to Examples and Comparative Examples. However, the present invention is not limited to these Examples.

Example

Improved Blade

Figure 2:
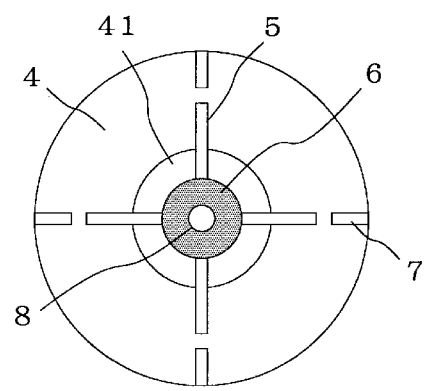
FIG. 2 is a sectional view as viewed in the direction of arrows I-I of the column-type solid-liquid countercurrent contact apparatus in FIG. 1.

A washing process of an aqueous slurry (PPS slurry) containing polyphenylene sulfide (PPS) particles is performed using the column-type solid-liquid countercurrent contact apparatus shown in FIGS. 1 and 2.

The PPS slurry used in Examples and Comparative Examples is prepared in such a way that the PPS particles are separated from a reaction liquid containing PPS polymers after a polymerization reaction, and the PPS particles washed with acetone and recovered are then turned into slurry again with an aqueous solvent.

The column-type solid-liquid countercurrent contact apparatus has an overall height of 1325 mm, and includes the column top part 1 having an inner diameter of 700 mm, the column body part 2 having an inner diameter of 310 mm and formed of an acrylic resin plate, and the inside of which is visible, and the column bottom part 3.

The column body part 2 is divided into the five stirring chambers 21 to 25. Each of the stirring chambers has an inner diameter D of 310 mm, and a height H of 116.3 mm (H/D=0.375). The ring-shaped partitioning plate 4 having the communication opening 41 with the inner diameter of 140 mm is provided between the stirring chambers. Four baffles 7 having a breadth of 15.5 mm and a height of 39 mm are fixed to the ring-shaped partitioning plate 4 at four positions of an inner wall of each stirring chamber at 90° intervals so as to extend in the height direction. The stirring shaft 8 having an outer diameter of 20 mm is provided by passing through the communication opening of the ring-shaped partitioning plate of each stirring chamber, and is rotated by a motor placed on an upper surface of the column top part.

In each stirring chamber, four flat paddle blades 5 as the paddle blades are fixed to the stirring shaft 8 at 90° intervals at a position of 25 mm upwardly away from the ring-shaped partitioning plate 4 and extending up to the height of 41 mm. The flat paddle blade 5 has a stirring blade diameter (as a total of the lengths of the two paddle blades and the outer diameter of the stirring shaft) of 232.5 mm, and a blade width of 15.5 mm. The circular disc 6 made of SUS 340 having an outer diameter of 93 mm and a thickness of 2 mm is fixed to the stirring shaft 8 via a fixture (not shown) so as to contact an upper surface of each of the flat paddle blades 5.

The solid particle inlet 91 is provided at a lower part of the column top part 1, and the liquid outlet 94 is provided at an upper part of the column top part 1. A diameter of a lower portion of the column top part 1 is gradually decreased in a tapered manner so as to contact an upper portion of the column body part. A paddle blade (no reference number) having a stirring blade diameter of 232.5 mm is fixed to the stirring shaft 8 in the column top part 1. However, as described above, it is permissible for the column top part 1 not to include the stirring blade.

The column bottom part 3 is provided with the liquid inlet 92 and the processed product outlet 93. The processed product outlet 93 is provided at a lowermost bottom part. The diameter of a lower portion of the column bottom part 3 is gradually decreased in a tapered manner toward the processed product outlet 93.

Therefore, the column-type countercurrent contact apparatus is provided with a total of six countercurrent contact steps including the five stirring chambers in the column body part and the column bottom part.

When the stirring shaft 8 was rotated at the number of stirring rotations of 15 rpm using the above-described column-type countercurrent contact apparatus, the stirring power was 0.7 W/m$^3$. Under this stirring condition, as described above, the PPS slurry was supplied through the solid particle inlet 91 at a rate of 550 kg/h, and an ion-exchanged water was supplied through the liquid inlet 92 at a rate of 600 kg/h.

A composition of the PPS slurry was the PPS particles (dry basis) of 20 mass % having an average particle diameter of 520 μam, the ion-exchanged water of 64 mass %, and the acetone of 16 mass %.

By an action of the improved blades provided in each stirring chamber, that is, the flat paddle blades 5, to which the discs 6 are attached, and the four baffles 7, the PPS slurry and the water were stirred and mixed in each stirring chamber, and the PPS particles and the water in the slurry were brought into contact with each other. While the washing process was progressed, the PPS particles (the density of 1.35) having a larger density than the water were gently settled, and passed through the stirring chambers successively. A waste liquid was discharged through the liquid outlet 94 at 650 kg/h, and a washed slurry was discharged through the processed product outlet 93 at 500 kg/h. No PPS particles were seen in the waste liquid. Therefore, a washing bath ratio defined by a ratio of the washing liquid and the PPS particles in slurry was 1.91. Also, an acetone concentration (outlet acetone concentration) in a washed slurry liquid phase was 3.36 mass %, and washing efficiency was 30%.

Further, in the above-described apparatus, the number of stirring rotations was changed to 25 rpm and 34 rpm, and the stirring power and the washing efficiency were measured. Note that the washing efficiency ϵ was calculated from the following formula:

$$C_1=C_0*(1-\epsilon)^{(n-1)}$$

(in the formula, $C_0$ represents a concentration of an objective product in a slurry at an inlet of an apparatus, $C_1$ represents a concentration of the objective product in the slurry at an outlet of the apparatus, and n represents the number of steps of stirring chamber. In Example and Comparative Example, the objective product is acetone.)

A result of Example using the improved blade is shown in Table 1.

Comparative Example

Conventional Blade

Figure 3:
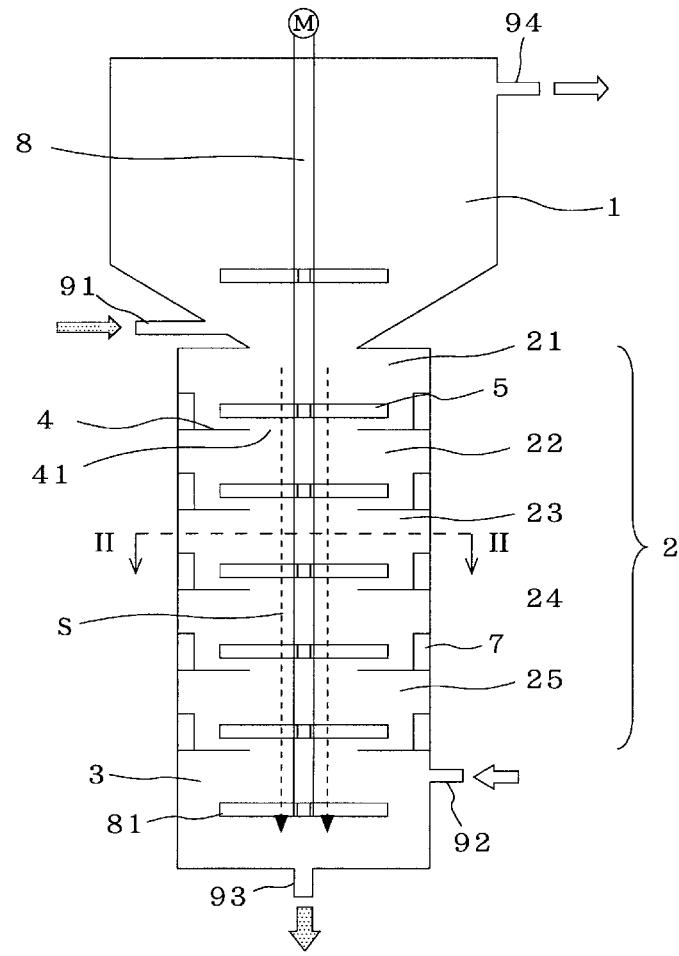
FIG. 3 is a schematic longitudinal sectional view of an example of a column-type solid-liquid countercurrent contact apparatus in which a conventional paddle blade is disposed.
Figure 4:
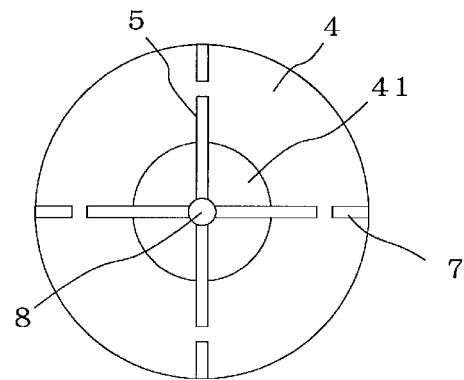
FIG. 4 is a sectional view as viewed in the direction of arrows II-II of the column-type solid-liquid countercurrent contact apparatus in FIG. 3.

The washing process was performed using the column-type countercurrent contact apparatus shown in FIGS. 3 and 4 instead of using the column-type countercurrent contact apparatus shown in FIGS. 1 and 2 in a similar manner to Example. The apparatus of FIGS. 3 and 4 is the same as the apparatus of FIG. 1 except that a conventional blade, that is, a flat paddle blade 5 without being provided with the disc 6 is provided as the stirring blade provided in each stirring chamber. Also, the number of stirring rotations is 22 rpm, 30 rpm, and 40 rpm in order to obtain almost the same stirring power as Example, and the stirring power and the washing efficiency were measured under each of the number of stirring rotations.

A result of Comparative Example using the conventional blade is shown in Table 1.

TABLE 1

|  | Example (improved blade) | | | Comparative Example (conventional blade) | | |
| --- | --- | --- | --- | --- | --- | --- |
| The number of stirring rotations (rpm) | 15 | 25 | 34 | 22 | 30 | 40 |
| Stirring power Pv (W/m$^3$) | 0.7 | 3.3 | 8.3 | 1.3 | 3.4 | 8.1 |
| Washing efficiency ε (%) | 30 | 33 | 38 | 26 | 34 | 35 |

It is understood that Example can realize the similar degree of stirring power with the smaller number of rotations of the stirring shaft when comparing Example with Comparative Example, Example using the column-type solid-liquid countercurrent contact apparatus provided with the improved blade (the flat paddle blade to which the disc is attached) of the present invention and Comparative Example using the column-type solid-liquid countercurrent contact apparatus provided with the conventional blade (the flat paddle blade without the disc). Further, the improved blade of Example can obtain higher washing efficiency with smaller stirring power in a small range of the stirring power under 1.5 W/m$^3$ (the stirring power was 0.7 W/m$^3$ in Example, whilst the stirring power was 1.3 W/m$^3$ in Comparative Example). It is assumed that, in Example using the improved blade, the PPS particles in the vicinity of the stirring shaft are very unlikely to be discharged by taking the short path, and stay in the stirring chamber for a relatively long time, whereby sufficient contact between the PPS particles and the washing liquid in the slurry is performed in the stirring chamber, and the washing efficiency is improved. On the other hand, in the washing process using the conventional blade in Comparative Example, the PPS particles in the vicinity of the stirring shaft were settled without being subjected to sufficient contact with the washing liquid, whereby the PPS particles repeated the movement from an upper stirring chamber to a lower stirring chamber, and were discharged from the column-type solid-liquid countercurrent contact apparatus. Accordingly, the PPS particles by taking the short path with insufficient washing process occurred.

INDUSTRIAL APPLICABILITY

The column-type solid-liquid countercurrent contact apparatus of the present invention is capable of realizing the high processing efficiency with the small stirring power while suppressing the occurrence of the short path, the stagnation, and the backward flow of the solid particles, whereby the countercurrent contact between the flow of the solid particles and the flow of the liquid can be continuously and efficiently performed. Therefore, it can be used for a unit operation mainly in the chemical industry such as washing, purification, extraction, impregnation, chemical reaction, and dissolution of the solid particles.

REFERENCE SIGNS LIST

1 Column top part
2 Column body part
21 to 25 Stirring chamber
3 Column bottom part
4 Ring-shaped partitioning plate
41 Communication opening
5 Flat paddle blade
6 Disc
7 Baffle
8 Stirring shaft
81 Flat paddle blade
91 Solid particle inlet
92 Liquid inlet
93 Processed product outlet
94 Liquid outlet
S Short path

The invention claimed is:

1. A column-type solid-liquid countercurrent contact apparatus comprising a column top part, a column body part, and a column bottom part, for causing solid particles and a liquid to be subjected to countercurrent contact, the column body part including:
   a plurality of stirring chambers connected in a vertical direction and mutually divided by each of ring-shaped partitioning plates having a communication opening in the center thereof,
   each of the plurality of stirring chambers including:
   a paddle blade fixed to a shared rotating shaft passing through the communication opening of each of the ring-shaped partitioning plates, and satisfying the following formulas (1) and (2):

(a blade diameter of the paddle blade)/(a diameter of the stirring chamber)≥0.65   formula (1)

(a blade width of the paddle blade)/(the diameter of the stirring chamber)≤0.10   formula (2);

at least one baffle extending in the vertical direction along an inner wall surface of the column body part; and
   a disc having a size covering at least a part of the communication opening positioned below the paddle blade, and being attached to the paddle blade so as not to have a gap between a circumference of the rotating shaft and the disc.

2. The column-type solid-liquid countercurrent contact apparatus according to claim 1, wherein
   (a) the column top part includes a solid particle inlet through which the solid particles or a slurry containing the solid particles are supplied,
   (b) the column top part includes, at an upper part than the solid particle inlet, a liquid outlet through which the liquid is discharged,
   (c) the column bottom part includes a liquid inlet through which a liquid for contact with the solid particles is supplied, and
   (d) the column bottom part includes, at a lower part than the liquid inlet, a processed product outlet through which a processed product is removed, the processed product resulting from the solid particles being subjected to contact process with the liquid for contact.

3. The column-type solid-liquid countercurrent contact apparatus according to claim 1, wherein the paddle blade is a flat paddle blade.

4. The column-type solid-liquid countercurrent contact apparatus according to claim 1, wherein the paddle blade is disposed at a lower half region of each of the stirring chambers.

5. The column-type solid-liquid countercurrent contact apparatus according to claim 1, wherein a ratio of an area of the communication opening of each of the ring-shaped partitioning plates in a horizontal direction to a cross-sectional area of each of the stirring chambers in the horizontal direction is within a range of 4 to 25%.

6. The column-type solid-liquid countercurrent contact apparatus according to claim 1, wherein the communication opening has a circular shape.

7. The column-type solid-liquid countercurrent contact apparatus according to claim 6, wherein the disc has a circular shape, and a diameter thereof is larger than that of the rotating shaft and has a ratio within a range of 0.3 to 1.2 times the diameter of the communication opening of each of the ring-shaped partitioning plates.

8. The column-type solid-liquid countercurrent contact apparatus according to claim 1, wherein a ratio H/D between a height H and an inner diameter D of each of the stirring chambers is within a range of 0.2 to 3.0.

9. The column-type solid-liquid countercurrent contact apparatus according to claim 1, wherein the solid particles are poly(arylene sulfide) particles.

10. A solid particle washing apparatus comprising the column-type solid-liquid countercurrent contact apparatus according to claim 1.

11. A poly(arylene sulfide) manufacturing apparatus comprising the column-type solid-liquid countercurrent contact apparatus according to claim 1.

12. A method of solid-liquid countercurrent contact of solid particles using the column-type solid-liquid countercurrent contact apparatus according to claim 1, wherein the method comprises inputting the solid particles into the apparatus such that the particles move downward through the stirring chambers while liquid moves upward through the stirring chambers.

13. A method of washing solid particles using the washing apparatus according to claim 10, wherein the method comprises inputting the solid particles into the apparatus such that the particles move downward through the stirring chambers while liquid moves upward through the stirring chambers.

14. A method of solid-liquid countercurrent contact of poly(arylene sulfide) particles using the column-type solid-liquid countercurrent contact apparatus according to claim 1, wherein the method comprises inputting the particles into the apparatus such that the particles move downward through the stirring chambers while liquid moves upward through the stirring chambers.

15. A method of manufacturing poly(arylene sulfide) using the column-type solid-liquid countercurrent contact apparatus according to claim 1, wherein the method comprises inputting poly(arylene sulfide) particles into the apparatus such that the particles move downward through the stirring chambers while liquid moves upward through the stirring chambers.

16. A method of washing poly(arylene sulfide) particles using the washing apparatus according to claim 10, wherein the method comprises inputting the particles into the apparatus such that the particles move downward through the stirring chambers while liquid moves upward through the stirring chambers.

* * * * *